(12) United States Patent
Schwenn et al.

(10) Patent No.: US 11,723,787 B2
(45) Date of Patent: Aug. 15, 2023

(54) MULTI-COMPONENT HIP ORTHOSIS

(71) Applicant: Orthomerica Products, Inc., Orlando, FL (US)

(72) Inventors: Shannon R. Schwenn, New Smyrna Beach, FL (US); Jeremy T. Schulte, Mount Dora, FL (US); Benjamin G. Domb, Glencoe, IL (US); Nicole F. Weill, Ocoee, FL (US)

(73) Assignee: ORTHOMERICA PRODUCTS, INC., Orlando, FL (US)

( * ) Notice: Subject to any disclaimer, the term of this patent is extended or adjusted under 35 U.S.C. 154(b) by 1061 days.

(21) Appl. No.: 16/459,480

(22) Filed: Jul. 1, 2019

(65) Prior Publication Data

US 2020/0030179 A1    Jan. 30, 2020

Related U.S. Application Data

(60) Provisional application No. 62/692,308, filed on Jun. 29, 2018.

(51) Int. Cl.
*A61F 5/01*       (2006.01)
*A61F 7/00*       (2006.01)

(52) U.S. Cl.
CPC ...... *A61F 5/0102* (2013.01); *A61F 2007/004* (2013.01); *A61H 2201/0192* (2013.01);
(Continued)

(58) Field of Classification Search
CPC ............. A61F 5/0102; A61F 2007/004; A61F 2007/0023; A61F 2007/0054; A61F 5/0193; A61F 2005/0132; A61F 2005/0137; A61F 2005/0144; A61F 2005/0158; A61F 2005/016; A61F 2005/0162;
(Continued)

(56) References Cited

U.S. PATENT DOCUMENTS 5,865,841 A * 2/1999 Kolen .................. A61H 9/0078
607/104
2005/0283102 A1* 12/2005 Schwenn .............. A61F 5/0193
602/5

(Continued)

FOREIGN PATENT DOCUMENTS

EP       1068846 A1 *  1/2001  ........... A61F 5/0193
EP       1159940 A2 * 12/2001  ........... A61F 5/0125

*Primary Examiner* — Rachael E Bredefeld
*Assistant Examiner* — Seth R. Brown
(74) *Attorney, Agent, or Firm* — Snell & Wilmer LLP

(57) ABSTRACT

Our design provides a moderate control of abduction and adduction without requiring tools. This can be accomplished with a first push button 5, shown in FIG. 1, for a hip adjustment of both abduction and adduction between a hip shell 2 and a hip hinge assembly that provides release of locking pins for setting the flexion and extension movement of the user's leg. A second push button 6 provides abduction and adduction between the hip hinge assembly 1 and a thigh supporting unit.

To facilitate an initial vertical adjustment, we provide a flexible plastic spacer 7 with circular openings extending through the spacer between the leg adjuster and the upper thigh support pad. The flexible plastic spacer 7 enables an initial adhesion between the hook and nap material through openings in the flexible plastic spacer 7.

20 Claims, 8 Drawing Sheets

(52) U.S. Cl.
CPC ........... *A61H 2201/0214* (2013.01); *A61H 2201/0242* (2013.01); *A61H 2201/165* (2013.01); *A61H 2205/088* (2013.01)

(58) Field of Classification Search
CPC ..... A61F 2005/0165; A61F 2005/0167; A61H 2201/0192; A61H 2201/0214; A61H 2201/0242; A61H 2201/165; A61H 2205/088; A61H 3/00; A61H 2003/007; A61H 1/0244; A61H 1/0255
See application file for complete search history.

(56) References Cited

U.S. PATENT DOCUMENTS

| | | | | |
|---|---|---|---|---|
| 2012/0289878 | A1* | 11/2012 | Schwenn | A61F 5/0193 602/23 |
| 2013/0178775 | A1* | 7/2013 | Paaske | A61F 5/0193 602/23 |
| 2014/0155964 | A1* | 6/2014 | Saggers | A61F 7/0097 607/104 |
| 2015/0230943 | A1* | 8/2015 | Marlin | A61F 2/68 623/47 |
| 2016/0015545 | A1* | 1/2016 | Petursson | A61F 5/0193 602/16 |
| 2018/0116852 | A1* | 5/2018 | Petursson | A61F 5/0109 |

* cited by examiner

MULTI-COMPONENT HIP ORTHOSIS

CROSS REFERENCE TO RELATED APPLICATIONS

This application claims the benefit and priority of U.S. Provisional Application No. 62/692,308, entitled "MULTI-COMPONENT HIP ORTHOSIS," filed on Jun. 29, 2018, the entire disclosure of which is hereby incorporated by reference herein in its entirety.

FIELD

A conventional hip orthosis frequently required tools to adjust a fit of the components to the patient.

SUMMARY OF THE INVENTION

Our hip orthosis is designed to be easily positioned and to enable adjustment and affixing of hip shells, while providing a lighter weight than a conventional hip orthosis, with a relatively low profile.

Our hip orthosis utilizes a waist band 12 that is flexible for adjustably conforming to the waist of a user having a first and second waist segments with a tightening cord 11 which can be a force multiplying connector cord for adjusting a displacement distance between the respective ends of the first and second waist segments, thereby enabling a lateral force to be applied to the user. The hip shell 2 of our hip orthosis is removably attached to the flexible waistband by a pair of flexible straps 13 with one of a hook and nap material for attaching to a surface of a flexible waistband 12 having a complimentary surface to enable an adhering of the hip shell 2 to the flexible waistband. Our first and second waist segments enable a tightening about the waist of the user to provide a lateral force to be applied to the user.

Our design provides a moderate control of abduction and adduction without requiring tools. This can be accomplished with a first push button 5, shown in FIG. 1, for a hip adjustment of both abduction and adduction between a hip shell 2 and a hip hinge assembly 4 that provides release of locking pins for setting the flexion and extension movement of the user's leg by rotation of control plates 22 (e.g., disks) with serrated edges in FIG. 7. We further provide a second push button 6 for hip adjustment of abduction and adduction between the hip hinge assembly 4 and a thigh supporting unit 1 which is attached to a leg adjuster bar, extending downward from the hip hinge assembly 4 in FIG. 7. The use of push buttons removes the requirements of tools.

A waist support unit 120 includes hip shell 2, shown in FIGS. 1 and 2, and a pair of flexible straps 13 support pad attached by one of a hook and nap material to a waist-band 12 encircling the waist of the patient, having a complimentary nap or hook material for adhering to the waist support unit 120 and a lower thigh support pad 14 configured to confirm to the user's thigh with a central space permitting vertical movement of the leg adjuster.

To facilitate an initial vertical adjustment, we provide a flexible plastic spacer 7 with circular openings extending through the spacer between the leg adjuster and a upper thigh support pad 14. We utilize one of a hook or nap material attached to the leg adjuster and the other of the hook or nap material is attached to the thigh support unit 1. The flexible plastic spacer 7 enables an initial adhesion between the hook and nap material through the openings in the flexible plastic spacer 7, as shown in FIG. 10.

This particular configuration of a flexible plastic spacer 7 enables further vertical movement by the plastic spacer to release the initial adhesion of the hook and nap material until the proper vertical position is reached. After a final adjustment to the proper vertical position, the flexible plastic spacer 7 can be removed to enable a firm attachment by a larger surface adhesion of hook and nap material to maintain the desired configuration of the hip orthosis without the requirement of tools, while providing moderate control of abduction and adduction and also control of flexion and extension by reducing any protrusion of a hip hinge that has occurred in hip orthoses in the past. Push button 5 above and push button 6 below the hinge enable a pivot placement, and the components that collectively form the hip orthosis 100, can be easily cleaned, both by the practitioner and ultimately during use by the patient. Reference can be made to FIGS. 1, 2 and 3 of our Drawings.

Additionally, our hip orthosis 100 can incorporate a cold therapy bladder 15 that can receive a flow of cold water to enable the application of cold therapy to the user while wearing the hip orthosis 100. Reference can be made to the Drawing of FIG. 8. A cold therapy pad 15 can utilize a metal frame that is relatively thin and pliable, such as aluminum, to thereby enable bending to accommodate, not only hoses for receiving and returning the cold fluid and an outer layer of foam is covered with a hook compatible cover, while a bottom layer, that will be positioned adjacent to the skin of the user, will also have foam with an outer surface covered with a terry type cloth.

BRIEF DESCRIPTION OF THE DRAWINGS

The features, aspects, and advantages of the embodiments will become better understood regarding the following description, appended claims and accompanying drawings.

DETAILED DESCRIPTION

Figure 8:
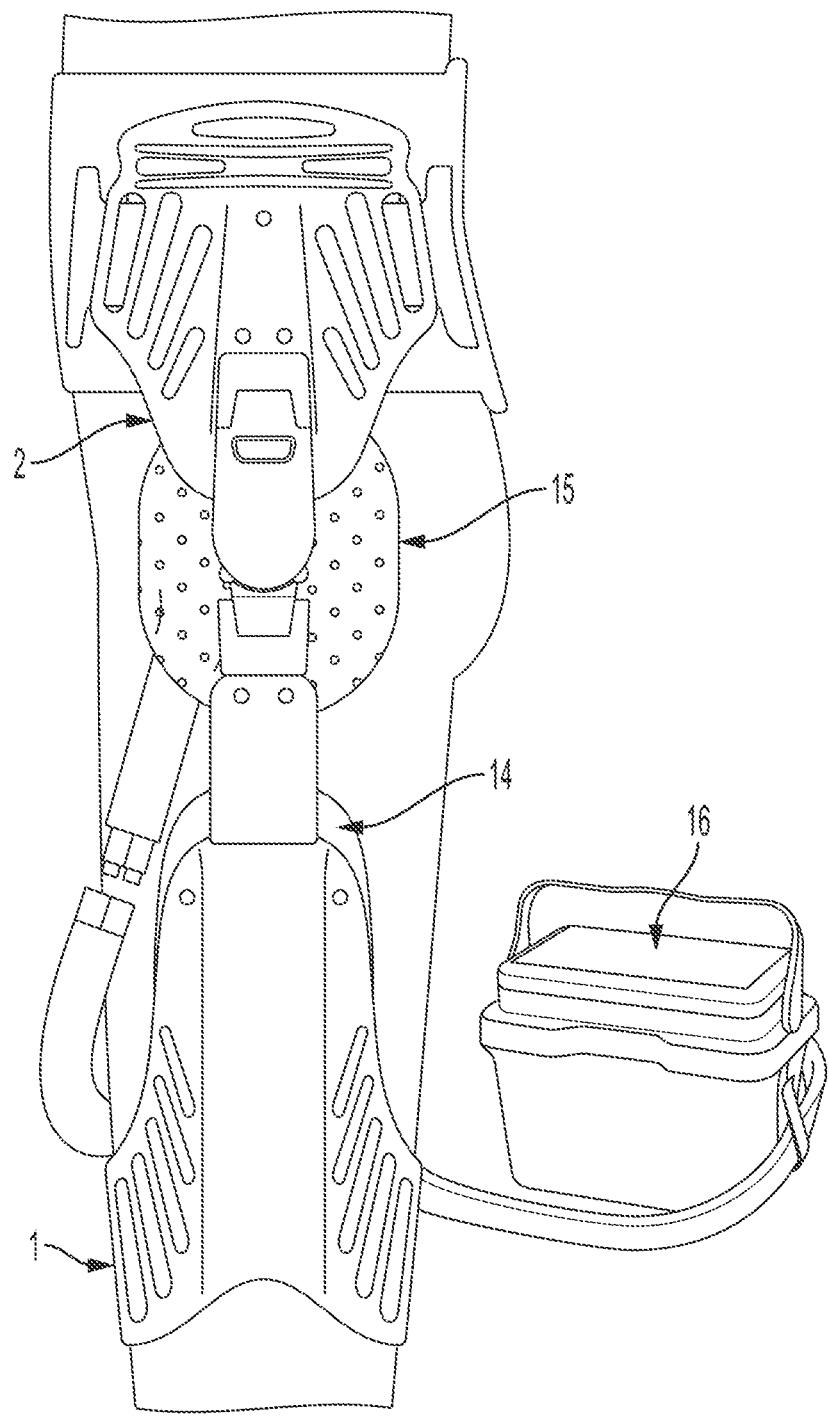
FIG. 8 discloses an application of cold therapy that can be provided on our hip orthosis. A cold therapy pad assembly, for example, of aluminum can be bent to conform to a treatment site of a patient with a terry cloth positioned to contact the user to moderate the application of a cold temperature of water delivered by a hose connected to a remote pump, connected to the source of cold water.
Figure 9D:
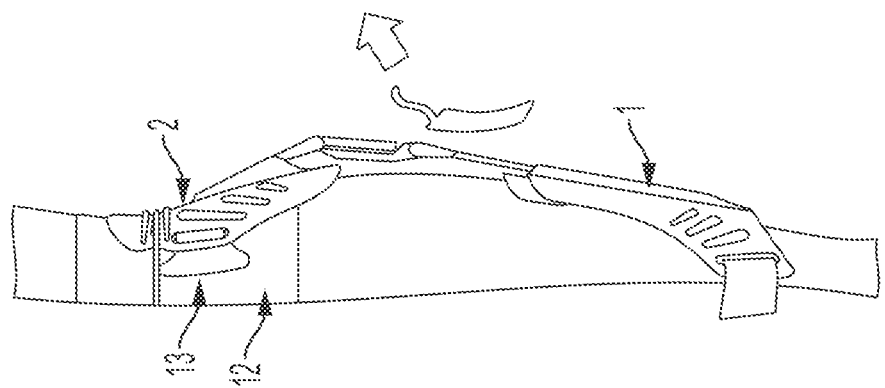
FIGS. 9A to 9D provides a donning sequence of the hip orthosis to a patient with a flexible plastic spacer 7 with circular openings that can enable vertical movement by releasing any attachment of nap and hook material through the circular openings for adjusting a vertical position of the hip orthosis.
Figure 9C:
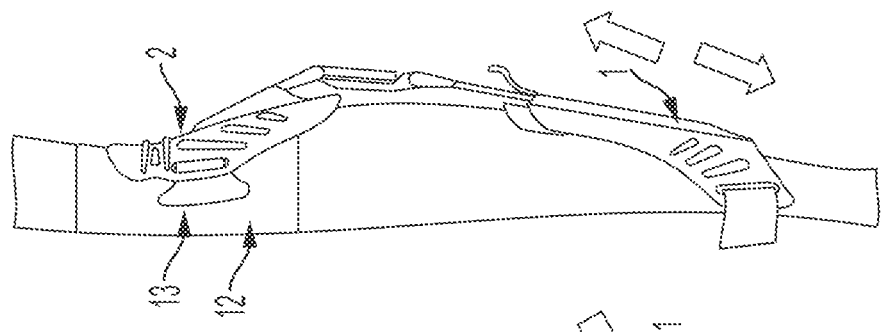
Figure 9B:
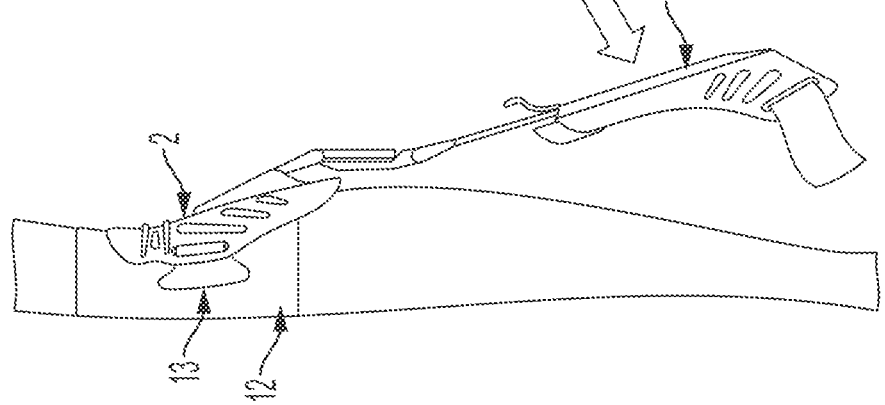
Figure 9A:
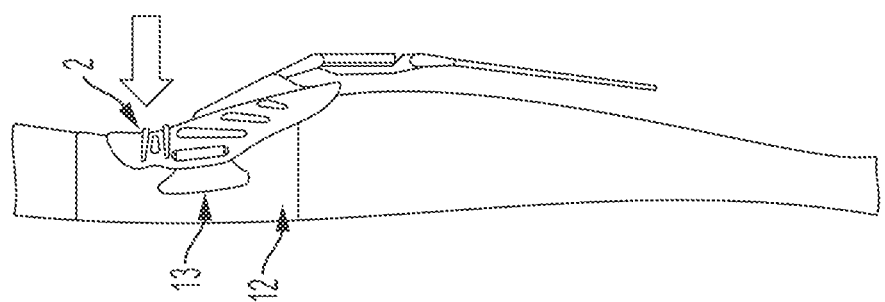
Figure 10B:
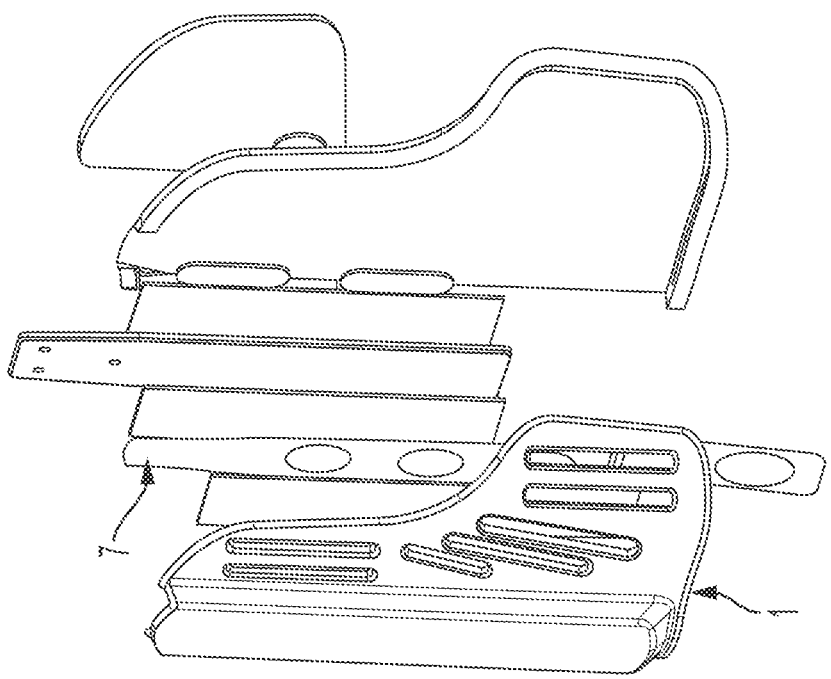
FIG. 10A shows an assembled thigh support pad and FIG. 10B is an exploded view of the components, including the flexible plastic spacer 7 with holes.
Figure 10A:
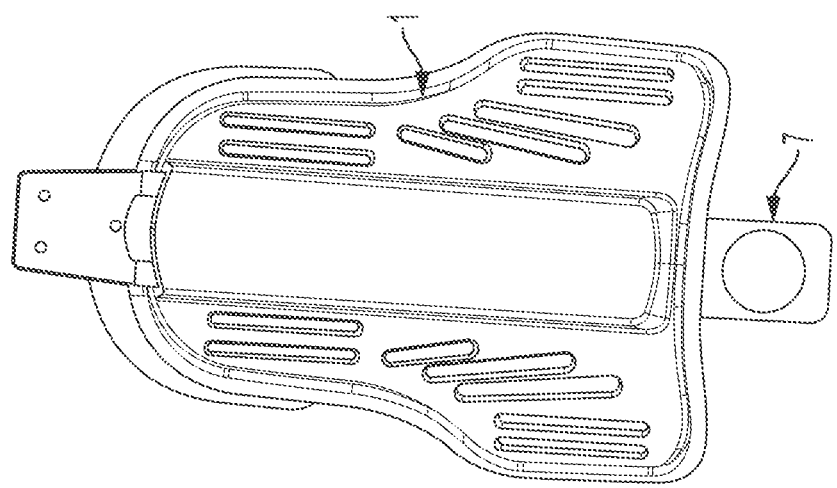

The cold therapy bladder 15 is positioned in FIG. 8 partly under the hip shell 2 and connected by a second hose extending from a cooler 16 to provide cold water to a side of the user's hip.

Thus, a cold therapy bladder, for example of aluminum, can be bent to conform to the surface of a patient that is to receive the cold therapy treatment. The top layer of the cold therapy bladder is compatible with the hooks of a VELCRO configuration for securing a position of a cold therapy bladder adjacent a treatment site for the patient. The bottom layer of foam is covered with a terry cloth designed to contact the user and to moderate the delivery of the cold treatment therapy to the user's body.

Figure 3:
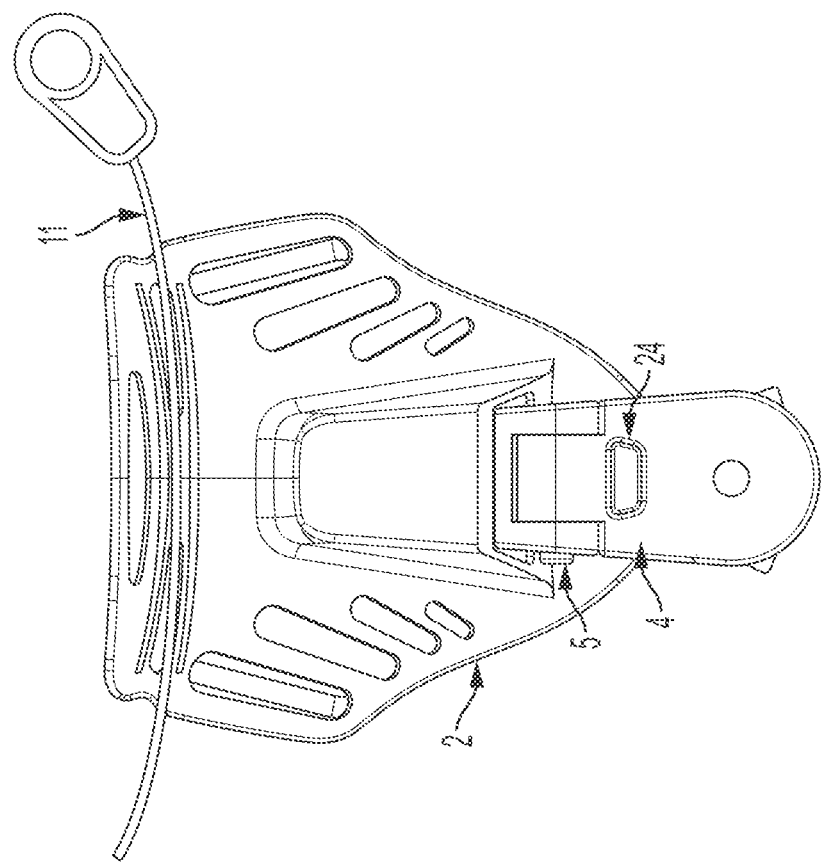
FIG. 3 is a side view of the hip shell 2 and a tightening cord 11 that can flex the hip shell 2 to conform to the patient's anatomy.

As can be seen in our Drawing, FIGS. 1-7B, the hip shell 2 has a series of open slots that facilitates conforming the hip shell 2 to the patient's autonomy with a tightening cord 11, shown in FIG. 3, that is capable of flexing the upper hip shell when tightened. Also seen on FIGS. 1 and 3 of our Drawings, we have push buttons 5 and 6 for providing both abduction and adduction adjustments.

Referring to FIGS. 1, 2, 7A to 7B, and 9A, 9B, 9C, and 9D, the manner of fastening the hip orthosis about the waist of a patient to the flexible waistband 12 is shown, along with positioning of the thigh component. The distal arm that can slide within a slot extending vertically on the thigh paddle permits an adjustment of the thigh shell height along the lower distal arm. Subsequently, removal of a flexible plastic spacer 7, when a desired positioning of a thigh shell height has been accomplished, permits a more permanent adhesion between the leg adjuster and the thigh shell.

Figure 6:
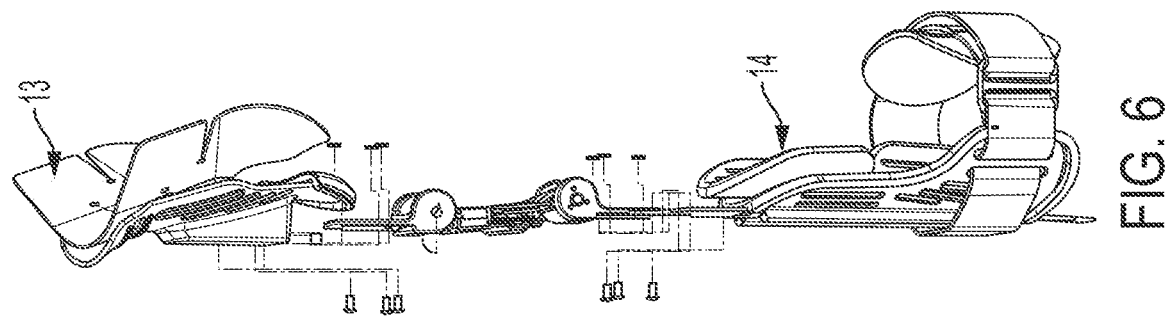
FIG. 6 is an exploded view of the components of our hip orthosis.
Figure 5:
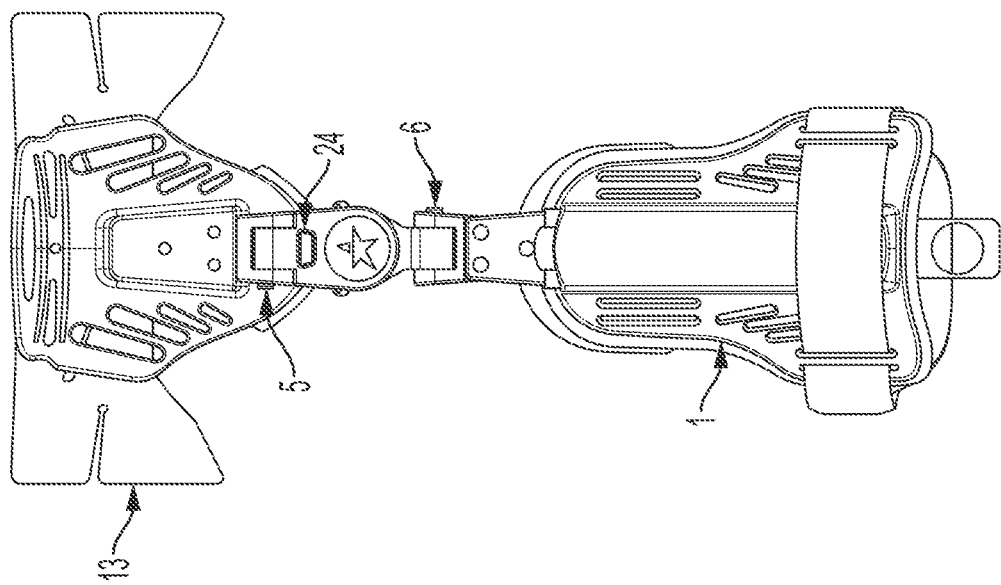
FIG. 5 is a side view of a hip shell 2 that can be attached to the waist band by hook and nap material and a lower thigh support shell 1 configured to conform to the user's thigh with a central space for permitting vertical movement of a leg adjuster.
Figure 7B:
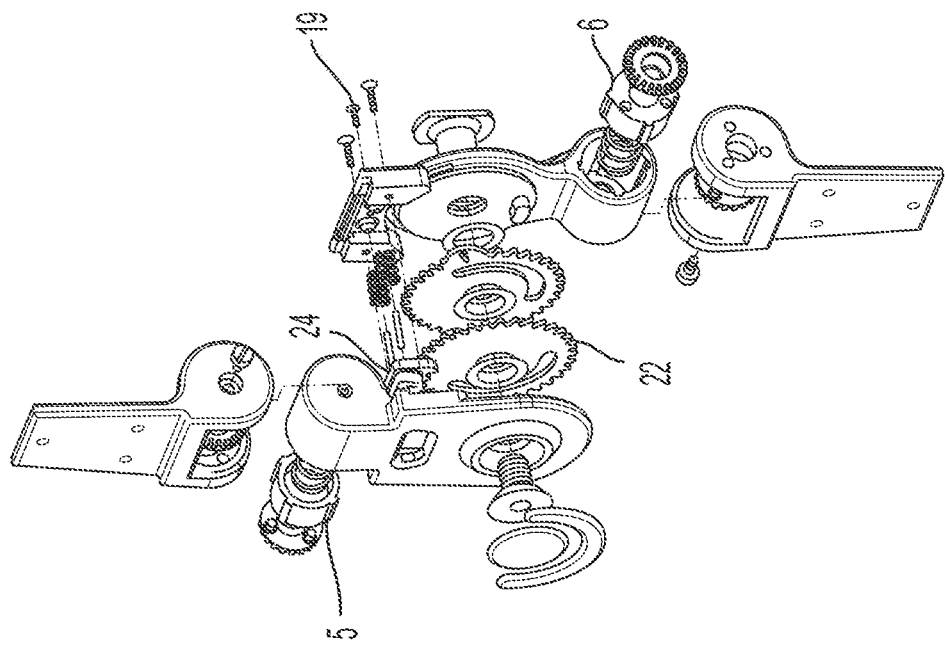
FIG. 7A is a view of the outside of the thigh shell 1 and FIG. 7B is an exploded view of the component parts, including rotatable control plates 22 that provide hip adjustment of abduction and adduction. A screw 19 can lock a trapezoidal button 24 to prevent any movement of the rotatable control plates 22 by the patient.
Figure 7A:
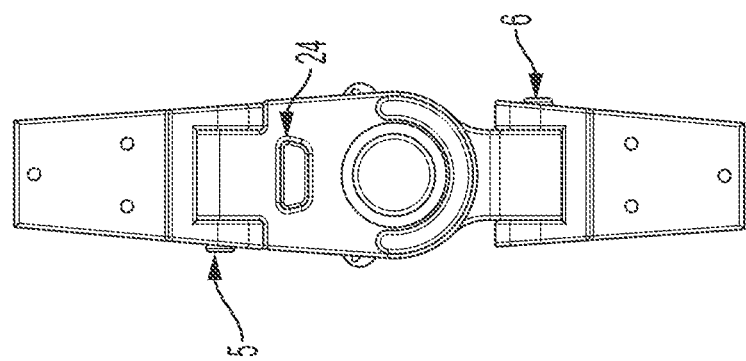

As can be appreciated, exploded views of our hip orthosis and individual components can be found in FIGS. 6 and 7A to 7B of our Drawings and the assembled configurations of our hip orthosis can be seen in FIGS. 1, 2, 5, and 6, that provides different relative points of view of our hip orthosis components. An exploded view of the components forming our hip orthosis can be seen in FIG. 6, with assembled views of the hip orthosis being seen in FIGS. 1, 2, 5, and 6.

Reference can be made to an adjustment comparison of the hip assembly length in FIG. 6 to appreciate the advantage of utilizing a removable flexible plastic spacer 7 with openings to permit the practitioner to relatively adjust the thigh support unit until a desired position is reached and then permanently adhered by pressing complimentary nap material and hook material together to permit a permanent position of the lower thigh support pad on the leg adjuster.

Figure 1:
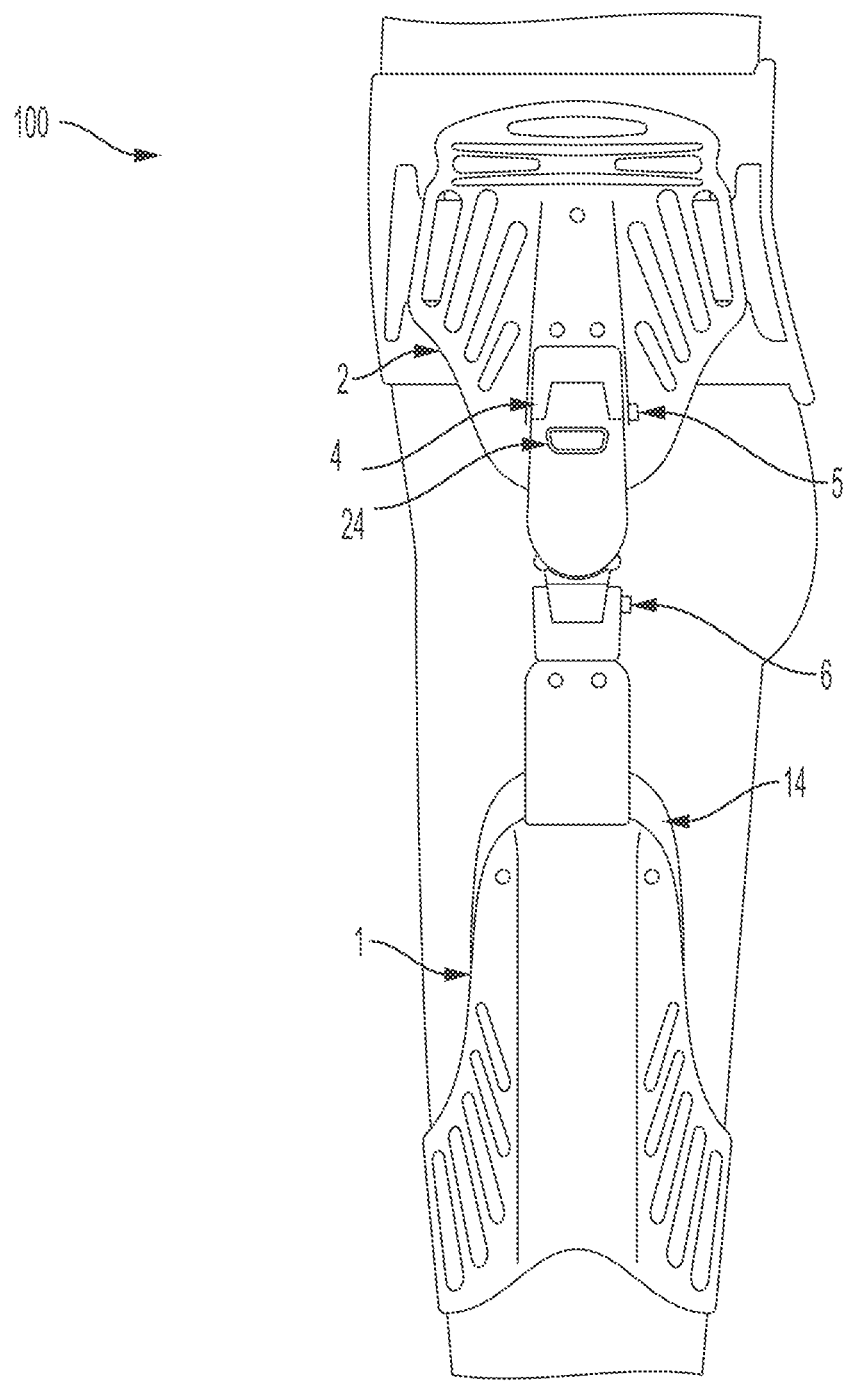
FIG. 1 is a side view of the hip orthosis 100 on a patient.
Figure 2:
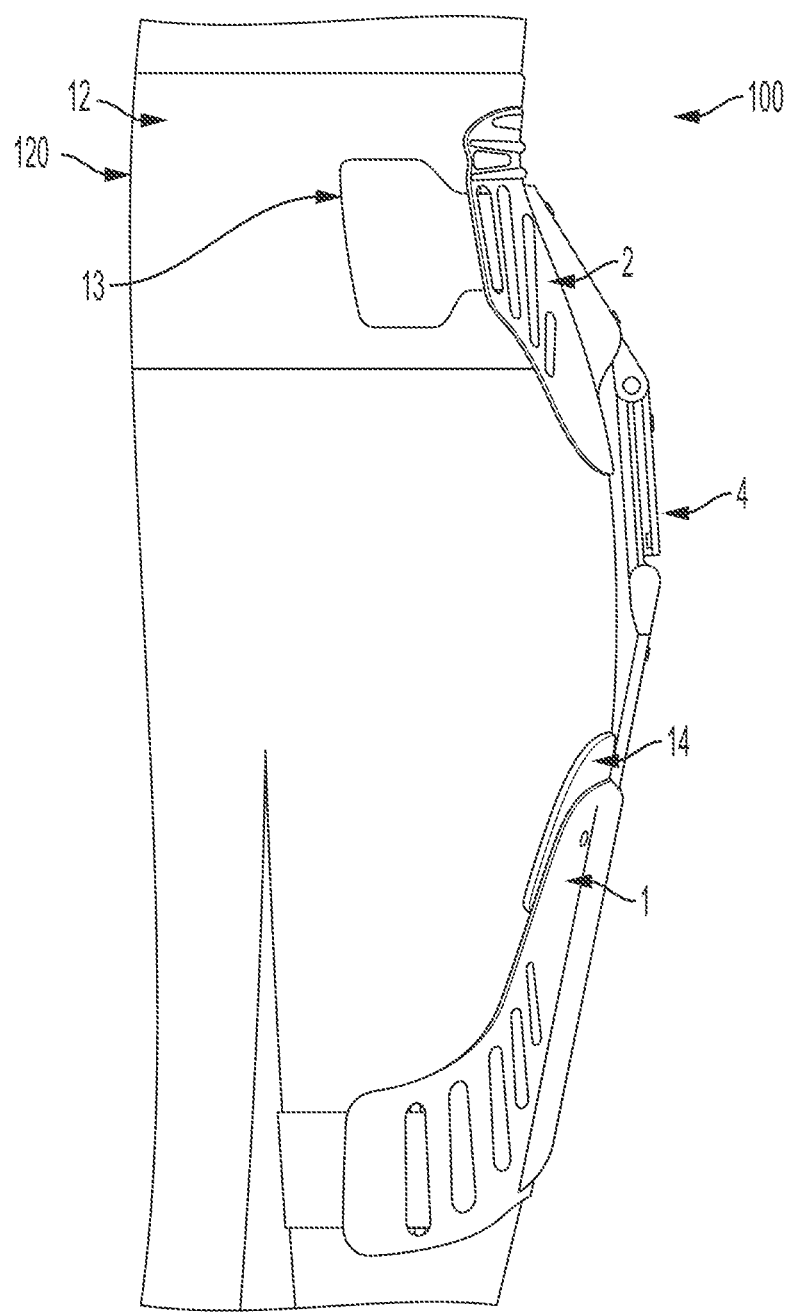
FIG. 2 is a front view of the hip orthosis 100 on a patient.
Figure 4:
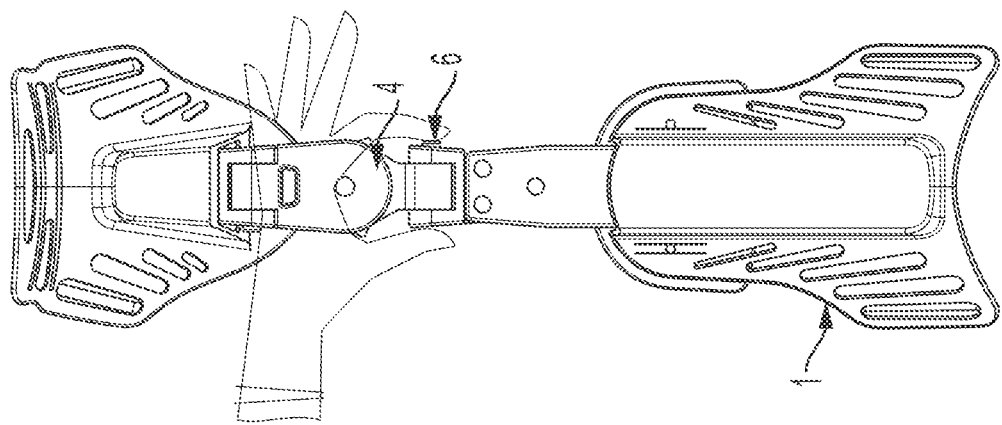
FIG. 4 is a side view of the hip orthosis wherein abduction and adduction adjustment can be made on the patient by squeezing a button and without the use of tools.

Referring to FIGS. 1, 2 and 9A, 9B, 9C, and 9D, a side view of the hip hinge assembly 4 enables a relative rotation upon pushing the trapezoidal button 24 on the hip hinge assembly 4 to permit a relative rotation for setting the flexion and extension movement for the user's leg. As can be appreciated, tools and fastening components that would have to be released or removed are not required to facilitate our adjustment. The configuration of a pair of control plates 22 that can be relatively rotated, when trapezoidal push button 24 is activated for hip adjustment of abduction and adduction as can be seen in FIGS. 1 and 7A to 7B. The leg adjustment structure can be seen in the Donning Sequence of FIG. 9A, 9B, 9C, and 9D, with an exploded view of the hip hinge assembly 4 shown in FIGS. 5, 6 and 10A to 10B.

FIGS. 7A to 7B includes a screw 19 that can be used to lock the trapezoidal push button 24 to prevent any movement of the rotatable control plates 22 so that the patient can not alter the settings recommended by the medical professional.

What is claimed is:

1. A hip orthosis for a leg of a user, comprising:
   a flexible waistband configured to conform to a waist of a user including first and second waist segments and a tightening cord for adjusting a displacement distance between respective ends of the first and second waist segments to tighten the first and second waist segments about the waist of the user to enable a lateral force to be applied to the user;
   a hip shell removably attached to the flexible waistband by flexible straps, the hip shell being configured to flex when tightened by the tightening cord;
   a first push button for hip adjustment of abduction and adduction between the hip shell and a hip hinge assembly having a push button release of locking pins for setting flexion and extension movement of the leg; and
   a second push button positioned below the first push button and the hinge assembly for hip adjustment of abduction and adduction between the hip hinge assembly and a thigh support unit which is attached to a leg adjuster extending downward from the hip hinge assembly.

2. The hip orthosis of claim 1, further comprising a flexible plastic spacer, extending below the thigh support unit with one or more circular openings to extend between the leg adjuster and an upper thigh support pad of the thigh support unit, wherein one of a hook or nap material is attached to the leg adjuster and the other of the hook or nap material is attached to the thigh support unit, the flexible plastic spacer enables an initial adhesion between the hook and nap material through the openings, while enabling a further vertical movement until a vertical position is reached and the flexible plastic spacer can be removed to provide a firm attachment over a larger surface adhesion of hook and nap material.

3. The hip orthosis of claim 1, further comprising a cold therapy bladder that can receive a flow of cold water is attached to the hip orthosis for enabling an application of cold therapy to the user.

4. The hip orthosis of claim 3, wherein the cold therapy bladder is formed of a thin and pliable metal frame that can be bent to conform to the user that is to receive the cold therapy.

5. The hip orthosis of claim 4, wherein the thin and pliable metal frame has top and bottom layers of foam attached to the metal frame.

6. The hip orthosis of claim 5, wherein the top layer of foam is covered with an outer layer that is compatible with adhering to hooks for securing a position of the cold therapy bladder.

7. The hip orthosis of claim 5, wherein the bottom layer of foam is covered with a terrycloth to contact the user.

8. The hip orthosis of claim 1, wherein the first push button is configured to set flexion and extension movement by rotation of a plurality of control plates.

9. The hip orthosis of claim 8, wherein the plurality of control plates are disks with serrated edges.

10. The hip orthosis of claim 1, wherein the thigh support unit includes an upper thigh support pad attached by one of a hook and nap material to a pad having a complimentary nap material or hook for adhering to the upper thigh support pad and a lower thigh support pad configured to conform to a thigh of the user with a central space for permitting vertical movement of the leg adjuster.

11. The hip orthosis of claim 1, wherein the hip shell comprises one of a hook and nap material for attaching to a surface of the flexible waistband with a complimentary surface to enable an adhering of the hip shell to the flexible waistband.

12. The hip orthosis of claim 1, wherein the tightening cord is a force multiplying connector cord.

13. The hip orthosis of claim 1, wherein the first push button and the second push button are positioned on a same side relative to the hip hinge assembly.

14. The hip orthosis of claim 1, wherein the first push button and the second push button are positioned on a same lateral side relative to the hip hinge assembly and the push button release is positioned on a different side than the first and second push buttons.

15. The hip orthosis of claim 1, wherein the first push button and the second push button are positioned on a lateral side and the push button release is oriented facing away from the user and is positioned on a side orthogonal to the first and second push buttons.

16. A hip orthosis for a leg of a user, comprising:
a flexible waistband configured to conform to a waist of a user including first and second waist segments and a cord for adjusting a displacement distance between respective ends of the first and second waist segments to tighten the first and second waist segments about the waist of the user;
a hip shell removably attached to the flexible waistband by flexible straps, the hip shell being configured to flex when tightened by the cord;
a first push button for hip adjustment of abduction and adduction between the hip shell and a hip hinge assembly having a push button release of locking pins for setting flexion and extension movement of the leg by rotation of a plurality of control plates; and
a second push button positioned below the hinge assembly for hip adjustment of abduction and adduction between the hip hinge assembly and a thigh support unit which is attached to a leg adjuster extending downward from the hip hinge assembly.

17. The hip orthosis of claim 16, further comprising:
a flexible plastic spacer extending below the thigh support unit with one or more circular openings to extend between the leg adjuster and an upper thigh support pad of the thigh support unit, the flexible plastic spacer configured to allow a further vertical movement until a vertical position is reached.

18. The hip orthosis of claim 16, wherein the first push button and the second push button are positioned on a lateral side and the push button release is oriented facing away from the user and is positioned on a side orthogonal to the first push button and the second push button.

19. The hip orthosis of claim 16, wherein the plurality of control plates are disks with serrated edges.

20. The hip orthosis of claim 16, further comprising a cold therapy bladder attached to the hip orthosis and configured to receive a flow of cold water for an application of cold therapy to the user.

* * * * *